(12) United States Patent
Bakstad

(10) Patent No.: US 8,513,395 B2
(45) Date of Patent: Aug. 20, 2013

(54) METHOD FOR THE SYNTHESIS OF ANTHOCYANINS

(75) Inventor: Einar Bakstad, Sandnes (NO)

(73) Assignee: Biosynth AS, Sandness (NO)

( * ) Notice: Subject to any disclaimer, the term of this patent is extended or adjusted under 35 U.S.C. 154(b) by 878 days.

(21) Appl. No.: 11/916,872

(22) PCT Filed: Jun. 15, 2006

(86) PCT No.: PCT/GB2006/002172
§ 371 (c)(1),
(2), (4) Date: Jul. 30, 2008

(87) PCT Pub. No.: WO2006/134352
PCT Pub. Date: Dec. 21, 2006

(65) Prior Publication Data
US 2009/0111975 A1    Apr. 30, 2009

(30) Foreign Application Priority Data

Jun. 15, 2005  (GB) .................................. 0512206.4

(51) Int. Cl.
C07H 15/00   (2006.01)
C07H 17/00   (2006.01)
C07G 3/00    (2006.01)

(52) U.S. Cl.
USPC ........................................... 536/8; 536/18.6

(58) Field of Classification Search
None
See application file for complete search history.

(56) References Cited

FOREIGN PATENT DOCUMENTS

| DE | 15 18 003 A1 | 2/1969 |
|---|---|---|
| DE | 21 41 527 A1 | 2/1973 |
| EP | 1215208 A2 | 6/2002 |
| GB | 1 425 049 A | 2/1976 |
| WO | WO 03/077577 A1 | 9/2003 |
| WO | WO 03/105766 A2 | 12/2003 |
| WO | WO 2004/096240 A1 | 11/2004 |
| WO | WO 2004/103986 A2 | 12/2004 |

OTHER PUBLICATIONS

McGhie, J. Agric. Food Chem. 2003, 51, 4539-4548.*
Protecting Groups & Carbohydrates Notes, 2003, obtained from www.alchemyst.f2o.org.*
Jurd, J. Am. Chem. Soc., 81, 4606 (1959).*
Gill et al. Eur J Med Chem (1996), 31, 847-859.*
Wamser, Portland State University, Organic Chemistry I class notes, Fall 1999.*
Fuji et al. Chem. Pharm. Bull. 26(10), 1978, 3218-3222.*
Reynolds et al. J. Chem. Soc.1934, 1039-1043.*
Dangles, O. et al. (1994) "Synthesis of 3-methoxy- and 3-(β-d-glucopyranosyloxy) flavylium ions. Influence of the flavylium substitution pattern on the reactivity of anthocyanins in aqueous solution" *Helvetica Chimica Acta* 77:1595-1610.
Howton, D.R. et al. (1954) "A new synthesis of dl-arterenol" *J. Amer. Chem. Soc.* 77:2896-2897.
Macchia, B. et al. (1986) "Conformational effects on the activity of drugs. 11. Stereostructural models for the direct activiation of the α- andβ-adrenergic receptor" *J. Med. Cham.* 29:740-747.
Mannich, C. et al. (1911) "Uber eine syntheses von α-aminoketonen mittels hexamethylentetramin" *Chemische Berichte* 44: 1542-1552.
Schmidt, R. (1986) "New methods for the synthesis of glycosides and oligosaccharides—are there alternatives to the koenigs-knorr method?" *Angew. Chem. Int. Ed. Engl.* 25:212-235.
Temple, D.L. et a. (1976) "Adrenergic sulfonanilides.4. Centrally active β-adrenergic agonists" *J. Med. Chem.* 19:626-633.
Tozuka, H. et al. (2005) "Synthesis of dihydroxypohenacyl glycosides for biological and medicinal study: β-oxoacteoside from paulownia tomentosa" *J. Wood Sci.* 51:48-59.
International Preliminary Report on Patentability, PCT/GB2006/002172, dated Jan. 8, 2008.
Corrigan, J. R. et al. 1945 "Preparation of N-Substituted 1-(p-Hydroxyphenyl)-2-aminoethanols" *Journal of the American Chemical Society* 67:21894-1896.
Chigurupati, N. et al. 2002 "Evaluation of red cabbage dye as a potential natural color for pharmaceutical use" *International Journal of Pharmaceutics* (Netherlands) 241(2):293-299.
Dangles, O. et al. 1994 "Synthesis of 3-methoxy- and 3- (β-D-glucopyranosyloxy) flavylium Ions. Influence of the Flavylium Substitution Pattern on the Reactivity of Anthocyanins in Aqueous Solution."*Helvetica Chemica Acta* 77(6):1595-1610.
Elhabiri, M. et al. 1998 "Synthesis, photochromism and metallic complexation of synthetic and natural anthocyanins." 2$^{nd}$ International Electronic Conference on Synthetic Organic Chemistry Sep. 1-30, 1998 poster abstract [dp092].
Galand, N. et al. 2002 "OPLC and AMD, recent techniques of planar chromatography: their interest for separation and characterization of extractive and synthetic compunds" *Fitoterapia* 73(2):121-134.
Halvorsen, B.L. et al. 2002 "A Systematic Screening of Total Antioxidants in Dietary Plants" *American Society for Nutritional Sciences* 132:461-471.

* cited by examiner

*Primary Examiner* — Layla Bland
(74) *Attorney, Agent, or Firm* — Knobbe, Martens, Olson & Bear, LLP

(57) ABSTRACT

The present invention relates to methods of preparing anthocyanins, and methods of preparing precursors of anthocyanins. The methods utilize a coupling reaction between a sugar and a suitable electrophilic precursor to form Eastern half intermediates that are then reacted with Western half intermediates to form the target anthocyanins. Some Eastern half intermediates and electrophilic precursors also form part of the invention.

11 Claims, No Drawings

METHOD FOR THE SYNTHESIS OF ANTHOCYANINS

RELATED APPLICATIONS

This application is a U.S. national Phase of International Application No. PCt/GB2006/002172, filed Jun. 15, 2006, designating the U.S. and published in English on Dec. 21, 2006 as WO 2006/134352. which claims the benefit of British application No. 0212206.4, filed Jun. 15, 2005.

FIELD OF THE INVENTION

The present invention relates to a method of preparing anthocyanins, and a method of preparing a precursor of anthocyanins.

BACKGROUND OF THE INVENTION

Anthocyanins are glycosides of flavylium salts. Each anthocyanin thus comprises three component parts: the hydroxylated core (the aglycone); the saccharide unit; and the counter ion. Anthocyanins are naturally occurring pigments present in many flowers and fruit and individual anthocyanins are available commercially as the chloride salts, e.g. from Polyphenols Laboratories AS, Sandnes, Norway.

As individual compounds, anthocyanins have been proposed for use as antioxidants (e.g. as free radical scavengers) for treatment of the vascular system.

Uses of anthocyanins in lowering C-reactive protein levels, treating or preventing type 2 diabetes, treating or preventing cardiovascular problems, and lowering the risk of adverse side effects of hormone replacement therapy, are disclosed in international patent application publication No. WO 04/096240.

Anthocyanins occur naturally in various fruits and vegetables. Particularly suitable sources for anthocyanins are fruits such as cherries, bilberries, blueberries, blackcurrants, redcurrants, grapes, cranberries, strawberries and apples, and vegetables such as red cabbage. Bilberries, in particular *Vaccinium myrtillus*, and blackcurrants, in particular *Ribes nigrum*, are especially suitable. The berries of *V. myrtillus* contain fifteen monosaccharide anthocyanins, namely the aglycone:saccharide combinations of cyanidin, peonidin, delphinidin, petunidin and malvidin with glucose, galactose and arabinose. The currants of *R. nigrum* contain four anthocyanins, namely the 3-glucosides and 3-rutinosides of cyanidin and delphinidin.

Anthocyanin-containing products may be prepared from such natural sources. International patent application publication No. WO 03/039569 discloses a method of preparing anthocyanin-containing products. This method can be applied to extracts from fruit or vegetables.

Rather than obtaining anthocyanins or anthocyanin-containing compositions from natural sources, they may be prepared by synthetic methods. Synthetic methods provide an alternative route to extraction from natural sources and may be preferable for the production of large quantities of specific anthocyanins. Synthesis of anthocyanins may also ease the regulatory process and/or avoid supply problems if a specific anthocyanin or mixture thereof is to be used as a medicament. Thus, a synthetic route may allow greater control of the purity or exact composition of a potential pharmaceutically active product.

Known synthetic routes to flavylium ions may involve the coupling together of two halves, the so-called "Eastern" and "Western" portions of the molecule (see for example, D. D. Pratt, R. Robinson, *J. Chem. Soc.* 1923, 745; T. J. Nolan, D. D. Pratt, R. Robinson, *J. Chem. Soc.* 1926, 1968; S. Murakami, R. Robinson, *J. Chem. Soc.* 1932, 1537; W. Bradley, R. Robinson, *J. Chem. Soc.* 1932, 1541; L. Reichel, H. W. Doering, *Justus Liebigs Ann. Chem.*, 1957, 606, 137; A. R. Katrizky, P. Czerney, J. R. Levell, W. Du, *Eur. J. Org. Chem.* 1998, 2623; C. Michaelidis, R. Wizinger, *Helv. Chim. Acta* 1951, 34, 1761; K. Kokkinos, R. Wizinger, *Helv. Chim. Acta* 1973, 56, 983; K. Kokkinos, R. Wizinger, *Helv. Chim. Acta* 1973, 56, 985; K. Kokkinos, R. Wizinger, *Helv. Chim. Acta* 1973, 56, 987; F. Herstein, S. Von Kostanecki, *Ber. Dtsch. Chem. Ges.* 1899, 32, 318; A. Roque, C. Lodeiro, F. Pina, M. Maestri, R. Ballardini, V. Balzani, *Eur. J. Org. Chem.* 2002, 2699; and R. A. McCelland, G. H. McGall, *J. Org. Chem.* 1982, 47, 3730; O. Dangles, A. El Hajji, *Helv. Chim. Acta* 1994, 77, 1595).

The "Eastern" and "Western" portions of anthocyanins are terms in the art to the synthetic organic chemist.

For example, anthocyanins may be prepared by the following general method as illustrated in Scheme 1 in accordance with the pioneering work of Sir Robert Robinson (the first total synthesis of cyanidin 3-O-β-glucopyranoside chloride as reported in S. Murakami, A. Robertson, R. Robinson, *J. Chem. Soc.* 1931, 2665 and the first total synthesis of delphinidin 3-O-β-glucopyranoside chloride, as reported in T. M. Reynolds, R. Robinson, *J. Chem. Soc.* 1934, 1039. The first anthocyanin to be synthesized by total synthesis was pelargonidin 3-O-β-glucopyranoside chloride (A. Robertson, R. Robinson, *J. Chem. Soc.* 1928, 1460). To the best of the inventor's knowledge, the last total synthesis of anthocyanins was reported by O. Dangles, A. El Hajji, *Helv. Chim. Acta* 1994, 77, 1595).

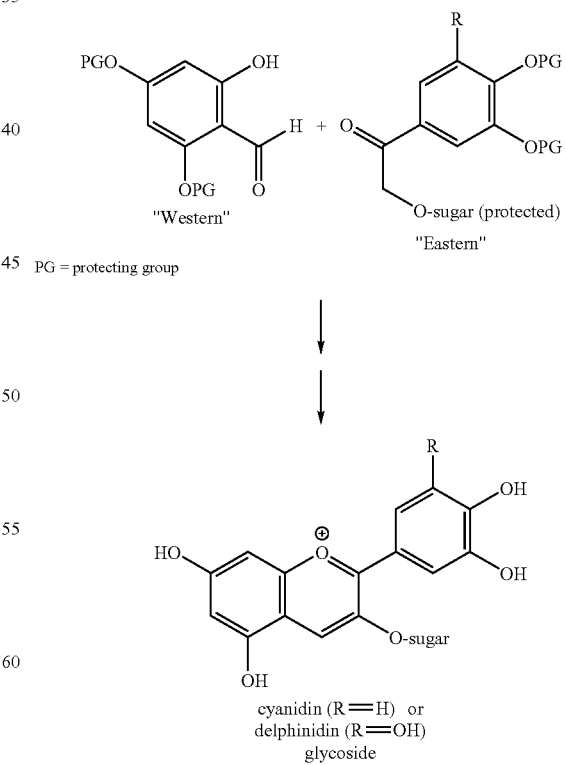

Scheme 1

However, known methods for preparing anthocyanins result in poor yields. Robinson used the Koenigs-Knorr reaction to prepare "Eastern" intermediates. This reaction requires the use of extremely dry conditions, results in low yields, and is not easily adaptable for use on a large scale. An attempt by the inventor of the present invention to synthesize an "Eastern" intermediate similar to one prepared by Robinson proceeded in only 8% yield (Scheme 2). This involved coupling 2-hydroxy-3',4'-diphenylmethylenedioxyacetophenone with 2,3,4,6-tetra-O-acetyl-α-D-glucopyranosyl bromide.

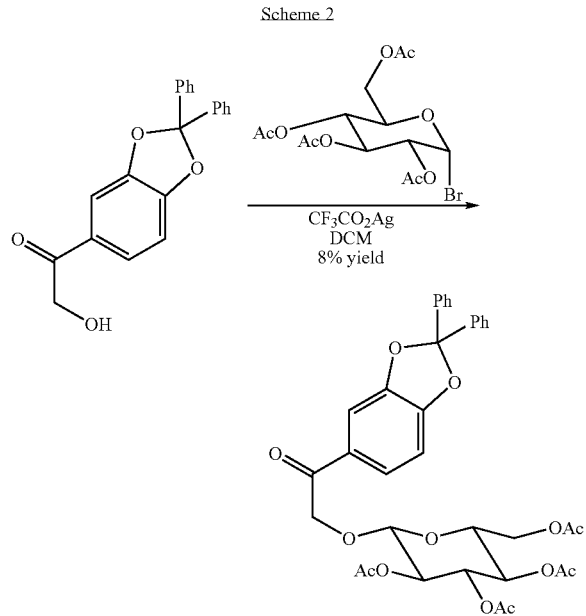

Scheme 2

Other known methods for preparing anthocyanins suffer from different drawbacks. For example, the Clemmensen reduction of rutin to give the corresponding anthocyanin, cyanidin 3-rutinose chloride (keracyanin), requires the use of toxic zinc amalgam (M. Elhabiri, P. Figueiredo, A. Fougerousse, R. Brouillard, *Tetrahedron Lett.*, 1995, 36, 4611).

DETAILED DESCRIPTION OF THE INVENTION

There is therefore still a need for alternative synthetic routes to anthocyanins, in particular a route that allows preparation of particular anthocyanins in a high yield and on a large scale. The present invention provides an improved method of preparation of a key "Eastern half" intermediate, thereby providing an improved synthesis of anthocyanins.

From a first aspect, the present invention provides a method for preparing an Eastern portion of an anthocyanin, comprising:

reacting an α-functionalized ketone starting material of general formula S-1:

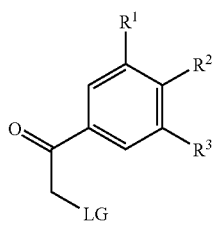

S-1 wherein LG is a leaving group;
$R^1$ is H, OMe or OPG;
$R^2$ is OPG;

and $R^3$ is H, OMe or OPG; and
each PG independently denotes a protecting group;
(throughout this specification PG denotes a protecting group and thus OPG denotes a protected hydroxy group; where PG is present in different parts of a compound it may, but does not necessarily, denote the same protecting group; and two adjacent OPG groups may optionally be taken together to form a cyclic moiety);
with a sugar anion of general formula:

$$XO^-$$

wherein $XO^-$ is an anion formed by removal of a proton from an anomeric oxygen atom of a sugar, any other hydroxy groups of the sugar being protected by suitable protecting groups; and
optionally removing some or all of the protecting groups;
to give an Eastern half intermediate of general formula E-1:

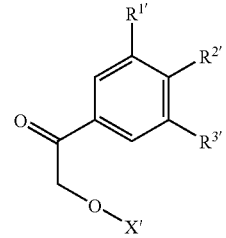

E-1 wherein $R^{1'}$, $R^{2'}$, $R^{3'}$ and $X'$ are each independently the same as $R^1$, $R^2$, $R^3$ and $X$ respectively, or are their deprotected analogues.

From a second aspect, the present invention provides a method for preparing an anthocyanin, comprising the above-described method for preparing an Eastern portion of an anthocyanin followed by:
optionally, in the event that any of $R^{1'}$, $R^{2'}$, $R^{3'}$ or $X'$ are the deprotected analogues of $R^1$, $R^2$, $R^3$ or $X$ respectively, reprotecting one or more of $R^{1'}$, $R^{2'}$, $R^{3'}$ and $X'$; and then
reacting the Eastern half intermediate of general formula E-1 or its reprotected derivative, with a Western half intermediate of general formula W-1:

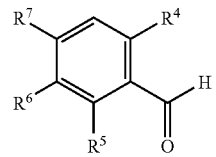

W-1 wherein either $R^4$ is OH, $R^5$ is OPG, $R^6$ is H, and $R^7$ is OH or OPG;
or $R^4$ is OH, $R^5$ is H, $R^6$ is OH or OPG, and $R^7$ is H;
thereby coupling intermediates E-1 and W-1, and optionally removing one, several or all protecting groups, to provide an anthocyanin product of general formula P-1:

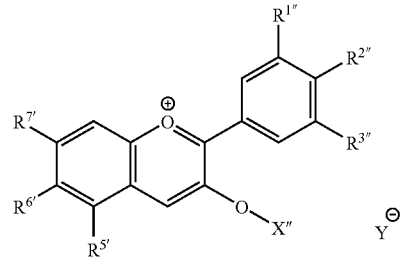

P-1 wherein $R^{1''}$, $R^{2''}$, $R^{3''}$, $X''$, $R^{5'}$, $R^{6'}$ and $R^{7'}$ are each independently the same as $R^{1'}$, $R^{2'}$, $R^{3'}$, $X'$, $R^5$, $R^6$ and $R^7$ respectively, or are their deprotected analogues; and $Y^-$ is a counterion, preferably a physiologically acceptable counterion.

Some of the compounds of formulae P-1 and S-1 are believed to be novel. Such compounds form a further aspect of the invention.

Anthocyanin compounds wherein none of the hydroxy groups are protected or derivatized exhibit desirable properties. However, the final deprotection step is optional since the protected anthocyanins may themselves be useful. Optionally, subsequent steps may be carried out, for example to replace protecting groups that have been lost and/or to interchange groups. For example, the hydroxy groups in P-1 may subsequently be derivatized to pharmacologically acceptable groups which can easily be removed ex vivo or in the body. In some cases, it may be advantageous to remove or change the protecting groups, for example for stability or toxicity reasons or otherwise. In particular, compounds in which one, several or all the hydroxy groups are derivatized to acetyl groups may exhibit desirable properties. However, acetyl groups can be used as protecting groups within the scope of the method of the present invention, regardless of whether they are present in the product P-1 or any subsequent product.

The definitions of $R^{1''}$, $R^{2''}$, $R^{3''}$, $R^{5'}$, $R^{6'}$ and $R^{7'}$ are such that the anthocyanin products of general formula P-1 include compounds comprising the aglycone cores of naturally occurring anthocyanins and their derivatives. However, the compounds P-1 may be naturally occurring anthocyanins or non-naturally occurring ("unnatural") anthocyanins. The definitions of $R^{1''}$, $R^{2''}$, $R^{3''}$, $R^{5'}$, $R^{6'}$ and $R^{7'}$ for the cores of some naturally occurring anthocyanins are as follows:

| aglycone | $R^{1''}$ | $R^{2''}$ | $R^{3''}$ | $R^{5'}$ | $R^{6'}$ | $R^{7'}$ |
|---|---|---|---|---|---|---|
| cyanidin | H | OH | OH | OH | H | OH |
| peonidin | H | OH | OCH$_3$ | OH | H | OH |
| delphinidin | OH | OH | OH | OH | H | OH |
| petunidin | OH | OH | OCH$_3$ | OH | H | OH |
| malvidin | OCH$_3$ | OH | OCH$_3$ | OH | H | OH |
| pelargonidin | H | OH | H | OH | H | OH |

The definitions of $R^1$, $R^2$, $R^3$, $R^{1'}$, $R^{2'}$, $R^{3'}$, $R^5$, $R^6$ and $R^7$ are preferably such that cyanidin or delphinidin anthocyanins or their derivatives can be prepared by the method of the present invention.

The present invention allows the production of anthocyanins by a convenient method and in high yield, due to the new and advantageous method for preparing the Eastern half intermediates of general formula E-1.

This method provides compounds of formula E-1 and P-1 in high yields and by a convenient and mild route which avoids toxicity problems associated with known methods. It is surprising that high yields of compounds of formula E-1 are obtained, in view of the presence of two electrophilic centres in the α-functionalized starting material S-1.

The coupling of a compound of general formula S-1 with a sugar anion of general formula $XO^-$ according to the present invention is a glycosylation reaction. In general, glycosylation reactions may result in the formation of a mixture of both α and β anomers or may allow access to only one anomer with respect to the sugar linkage. However, a further advantage of the glycosylation step of the present invention, compared to most other glycosylation methods, is that it can be controlled to result in the formation of either the α or the β anomer.

In the compound of formula S-1, any suitable leaving group LG may be used. The leaving group LG is preferably bromine, iodine, tosylate, brosylate, triflate, mesylate, or quaternary ammonium (e.g. $NR_3^+$, where each R is independently H or $C_{1-10}$ alkyl), more preferably bromine or iodine, most preferably iodine. The leaving group is chosen for its reactivity and compatibility, and the reaction works particularly well when bromine or iodine are used.

The sugar moiety $XO^-$ may be a mono-, oligo- or polysaccharide. Examples of suitable monosaccharides include glucose, galactose and arabinose. An example of a suitable disaccharide is rutinose (i.e. 6-rhamnosyl-glucose). Monosaccharides, such as glucose, are preferred, due to the activity and uptake profile of the resulting anthocyanins. Monosaccharides are also generally easier to work with. During the method of the present invention, all the hydroxy groups on the sugar moiety should carry protecting groups to avoid undesired side-reactions. Any other functional groups in the sugar moiety may also require suitable protection. The present invention covers the use of both D and L enantiomers of the sugar, but the use of the naturally occurring enantiomer is preferred. Particularly preferred sugars include D-glucose, D-galactose, D-arabinose and 6-L-rhamnosyl-D-glucose.

The sugar anion $XO^-$ may be present as a salt with any suitable cation which does not prevent the nucleophilic attack of $XO^-$ on the α-functionalized ketone starting material of general formula S-1. The salt may be prepared by reaction of the corresponding sugar XOH with a base, e.g. a hydride reagent. Suitable cations include cations of Group I metals, such as $Na^+$, in which case reaction of the sugar XOH with sodium hydride is a convenient way of obtaining the desired anion. Sodium hydride is advantageous because it is inexpensive and readily available. Other suitable cations include, but are not limited to, potassium and lithium. Preparing the $XO^-$ moiety in situ (i.e. in the presence of the α-functionalized ketone S-1) reduces the possibility of unwanted side reactions.

The present invention allows the preparation of both α- and β-stereoisomers with respect to the sugar linkage. Naturally occurring anthocyanins generally have a β-(equatorial) linkage, and the preparation of equatorially linked (β-) stereoisomers using the method of the invention is preferred. Preparing the $XO^-$ anion by using a strong base such as sodium hydride results in the Eastern intermediate having the same configuration as the XOH precursor (i.e. the kinetic product is formed). Thus it is necessary to use a β-stereoisomer of an XOH precursor and to prepare the $XO^-$ anion by using a strong base such as sodium hydride in situ, to provide the β-stereoisomer of intermediate E-1. Use of the α-anomer of the XOH precursor with a strong base will lead to formation of the α-linked intermediate E-1.

Use of a weaker base to generate the $XO^-$ anion will tend to lead to a mixture of the α- and β-anomers being formed. If the XO- anion is allowed to equilibrate, then the thermodynamic anomer (generally the α-anomer) will predominate.

The use of a compound of formula S-1 which is a potent electrophile also favours the kinetic product. Use of a poor electrophile results in longer reaction times, promoting ring opening of the sugar and favouring formation of the thermodynamic product. Thus, the kinetic product is obtained in the highest yields (relative to the thermodynamic product) by using a strong base such as sodium hydride and a potent electrophile such as an iodo-compound (i.e. compounds of formula S-1 wherein LG denotes I).

$Y^-$ may be any suitable counterion, preferably a physiologically acceptable counterion such as chloride, ascorbate, sulphate, phosphate, succinate, fumarate, malate, maleate or citrate. Preferably the counterion is a fruit acid anion, in particular a citrate, since these have noticeable taste benefits. Chloride ions are also preferred. Known procedures for coupling Eastern and Western intermediates include the use of an acid to inter alia quench the reaction and/or remove protecting groups, and an appropriate acid may be chosen so that the desired counterion is incorporated in the product. Optionally, anion exchange may be carried out if desired.

Methods to couple Eastern-half intermediates such as E-1 with Western-half intermediates such as W-1 are known in the art, and are described in, for example, A. Robertson, R. Robinson, *J. Chem. Soc.* 1928, 1460; S. Murakami, A. Robertson, R. Robertson, *J. Chem. Soc.* 1931, 2665; A. Leon, A. Robertson, R. Robinson, T. R. Seshadri, *J. Chem. Soc.* 1931, 2670; L. F. Levy, T. Posternack, R. Robinson, *J. Chem. Soc.* 1931, 2701; L. F. Levy, R. Robinson, *J. Chem. Soc.* 1931, 2715; K. E. Grove, R. Robinson, *J. Chem. Soc.* 1931, 2722; E. L. Fonseka, R. Robinson, *J. Chem. Soc.* 1931, 2730; A. Leon, R. Robinson, *J. Chem. Soc.* 1931, 2732; L. F. Levy, R. Robinson, *J. Chem. Soc.* 1931, 2738; R. Robinson, A. R. Todd, *J. Chem. Soc.* 1932, 2488; T. M. Reynolds, R. Robinson, *J. Chem. Soc.* 1934, 1039; O. Dangles, A. El Hajji, *Helv. Chim. Acta* 1994, 77, 1595.

As described above, protecting groups are used in the present invention, on some of the hydroxy groups in the Eastern and Western rings and in the sugar moiety. The use of protecting groups is well known in the art (see for example, T. W. Greene and P. G. M. Wuts, Protective Groups in Organic Synthesis, 3rd Edn., John Wiley & Sons). The skilled person will be aware of particular groups available for protecting hydroxy groups and other functional groups, and the conditions under which protection and deprotection can occur. Any suitable protecting groups may be used in the process of the invention. Any such protecting groups should remain on the hydroxy groups during at least part of the first step of the process (preparation of Eastern intermediate), so that nucleophilic attack of the sugar oxyanion (XO$^-$) onto the α-functionalized ketone can occur without too many unwanted side reaction(s). To the extent that the protecting groups used in the first step are lost or are unsuitable for the second step (coupling of Eastern and Western intermediates), protecting groups should be incorporated so that coupling can occur without too many unwanted side reaction(s). It is of course preferable to use the same protecting groups for both steps, so as to minimize the complexity of the synthesis. The protecting groups should be capable of being removed during or subsequent to the second step if desired.

Suitable protecting groups for hydroxyl groups in the method of the invention include, but are not limited to, acyl groups (e.g. acetyl or benzoyl), which may be easily removed under basic conditions, and benzyl groups, which may be removed by hydrogenation. The use of benzyl protecting groups is particularly preferred for large scale synthesis due to their easy removal by hydrogenation. In all cases, the conditions for removing the protecting groups should be such that the anthocyanin product P-1 is not unduly damaged.

Vicinal diols may be protected by the formation of cyclic groups such as acetals, ketals and orthoesters. Preferred cyclic groups include those shown below:

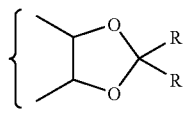

wherein each R independently denotes, for example, H, alkyl (e.g. $C_1$-$C_6$ alkyl), aryl (e.g. phenyl), or alkoxy (e.g. $C_1$-$C_6$ alkoxy). For example, protection of vicinal diols as the diphenylmethylenedioxy derivative:

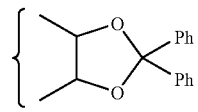 [SMILES: CC1OC(c2ccccc2)(c2ccccc2)OC1C]

may be carried out by reaction of the vicinal diol with dichlorodiphenylmethane, for example in refluxing toluene. Following coupling, such protecting groups may be removed by reaction with aqueous acid.

Because methods of coupling Western and Eastern intermediates usually involve an acidic reaction step, protecting groups which are not acid-labile, or which are only slightly acid-labile, may be preferred. For example, some acetate protecting groups may be lost during the coupling due to their acid-lability whereas benzoyl esters are more resistant to acid hydrolysis. Nevertheless, acid-labile protecting groups may be employed. For example, as is exemplified below, some of the hydroxy groups on the Western half intermediate and the sugar may be converted to acetate groups, and the hydroxy groups on the Eastern portion may be converted to a diphenylmethylenedioxy group. The protecting groups can then be simply hydrolysed during or following coupling of the Eastern half and Western half intermediates to release the free hydroxy groups.

$R^{2'}$ or $R^{2''}$ preferably denote a hydroxy group or a group that is hydrolyzed under basic conditions to release a hydroxy group. The inventor has found that this enhances the stability of the anthocyanin product P-1 and avoids side reactions under basic conditions. $R^{2'}$ or $R^{2''}$ may, for example, denote OH or OCOCH$_3$.

It is advantageous to protect the vicinal diol on the aromatic ring of the Eastern half of the anthocyanin (i.e. the substituents $R^2$ and $R^3$) by converting this vicinal diol to a diphenylmethylenedioxy group. This protecting group has an appropriate level of acid stability to withstand the reaction conditions whilst being removable under mild conditions.

Preferred combinations of moieties in starting material S-1 include the following (Ac denotes acetyl, Bn denotes benzyl, and Bz denotes benzoyl in accordance with normal organic chemistry abbreviations):

| combination no. | $R^1$ | $R^2$ | $R^3$ |
|---|---|---|---|
| 1 | H |  | OCPh(Ph)O |
| 2 | H | OAc | OAc |
| 3 | H | OBn | OBn |
| 4 | H | OBz | OBz |
| 5 | OAc |  | OCPh(Ph)O |
| 6 | OAc | OAc | OAc |
| 7 | OBn | OBn | OBn |
| 8 | OBz | OBz | OBz |

Preferred combinations of moieties in Western intermediate W-1 include the following:

| combination no. | $R^4$ | $R^5$ | $R^6$ | $R^7$ |
|---|---|---|---|---|
| 1 | OH | OBz | H | OBz |
| 2 | OH | OBz | H | OH |

| combination no. | R⁴ | R⁵ | R⁶ | R⁷ |
|---|---|---|---|---|
| 3 | OH | OAc | H | OAc |
| 4 | OH | OAc | H | OH |
| 5 | OH | OBn | H | OBn |
| 6 | OH | OBn | H | OH |
| 7 | OH | H | OH | H |
| 8 | OH | H | OBz | H |
| 9 | OH | H | OAc | H |
| 10 | OH | H | OBn | H |

Preferred protecting groups for the hydroxy groups in XO⁻ include acetyl, benzyl and benzoyl.

Cyanidin anthocyanins may in one embodiment be prepared by the use of acetyl protecting groups on the Western half and sugar, and the use of diphenylmethylenedioxy protection on the Eastern half.

Delphinidin anthocyanins may in one embodiment be prepared by the use of acetyl protecting groups on the Western half and sugar, and the use of benzyl protection on the Eastern half.

The reaction of starting material of general formula S-1 with sugar anion XO⁻ to form Eastern half intermediate of general formula E-1 is preferably carried out under the following conditions. The reaction time and temperature are such that the reaction proceeds to a high conversion. For example, reaction times of 0-30 hours, preferably 5-20 hours, and temperatures of 0-50° C., more preferably 10-35° C., more preferably around room temperature, have been found to be suitable.

Preferably the starting material of formula S-1 and sugar of formula XOH are dissolved in a solvent and a base (e.g. a hydride reagent, preferably sodium hydride) is added to this solution, preferably in portions so that the reaction proceeds in a controlled manner, preferably under stirring. The reaction is preferably carried out in a reasonably polar solvent, under dry conditions. Suitable solvents include, for example, dimethyl sulfoxide (DMSO), tetrahydrofuran (THF), 1,2-dimethoxyethane (DME) and dichloromethane (DCM). Solvents which are polar or semi-polar, but which are not deprotonated in the presence of a strong base, are preferred due to the higher yields obtainable in these solvents. For example, care should be taken if an excess of NaH is used in DCM, as NaH can cause decomposition of DCM. Such decomposition can be minimized by keeping the reaction temperature low (e.g. at room temperature or below). Under the reaction conditions described in the experimental part, no significant decomposition of dichloromethane was observed despite the use of excess NaH.

In the coupling reaction, compounds of formula S-1 in which LG is Br or I have been found to be the most preferable starting materials, with the I compounds being particularly preferred. DME, THF and DCM are preferably used as solvents when using Br compounds, more preferably THF and DME, with DME being the most preferred solvent. The use of THF and DME as solvents resulted in higher yields during the coupling reaction using Br compounds (the use of DCM resulted in formation of by-products, resulting in lower yields). The reactivity of the I compounds in the coupling reaction has been found to be largely independent of the solvent, although DCM is preferably used for cost reasons and as it is easier to dry than THF or DME. Without wishing to be bound by theory, it is believed that iodide is a better leaving group than bromide, and that therefore a highly polar solvent is not required in order to promote the coupling reaction.

Starting materials of general formula S-1, Western half intermediates of general formula W-1, Eastern half intermediates of general formula E-1 and sugar anions of general formula XO⁻ are commercially available or obtainable via standard organic synthetic methods.

For example, the starting material of formula S-1 where R¹ is H can be prepared from the corresponding α-chloro ketone which is commercially available. One way of obtaining the starting material S-1 where R¹ is protected hydroxy starts from commercially available compounds based on gallic acid (3,4,5-trihydroxybenzoic acid). Protected XOH compounds are commercially available or easily preparable, for example by reaction of the corresponding XBr compounds with silver carbonate (C. M. McCloskey, G. H. Coleman, Organic Syntheses, Coll. Vol. 3, 434).

In accordance with preferred embodiments of the present invention, cyanidin-3-O-β-glucopyranoside chloride (1) and delphinidin-3-O-β-glucopyranoside chloride (9) were prepared according to the following reaction schemes (Schemes 3 and 4) and experimental methods. Compounds (3), (5), (10) and (11) used in these Schemes are believed to be novel, and form a further aspect of the invention.

Scheme 3

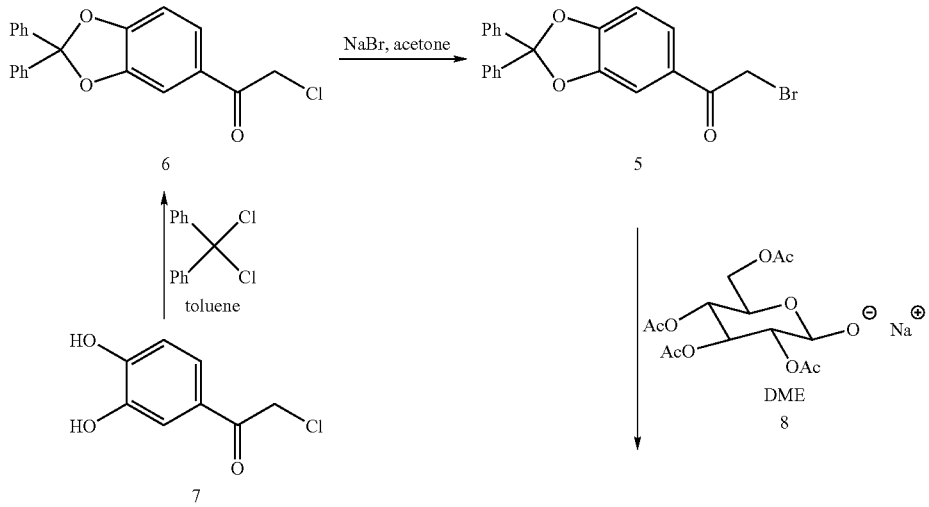

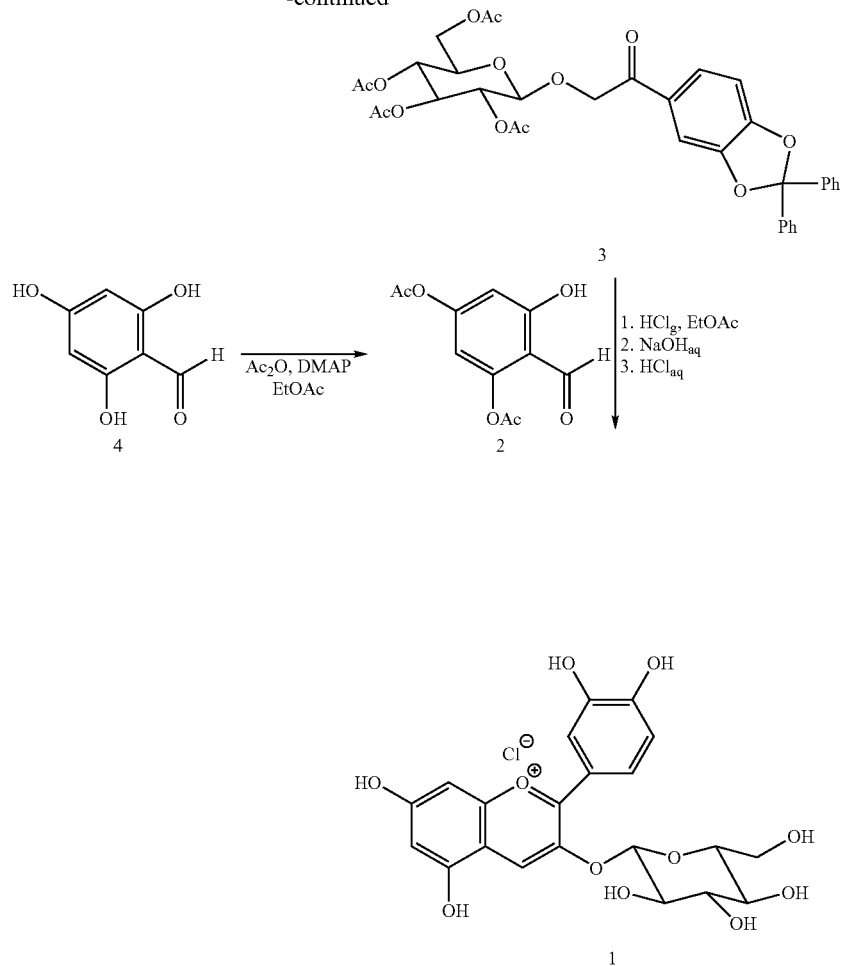
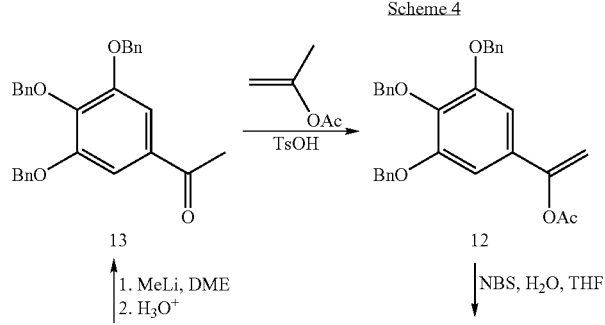
Scheme 4

-continued
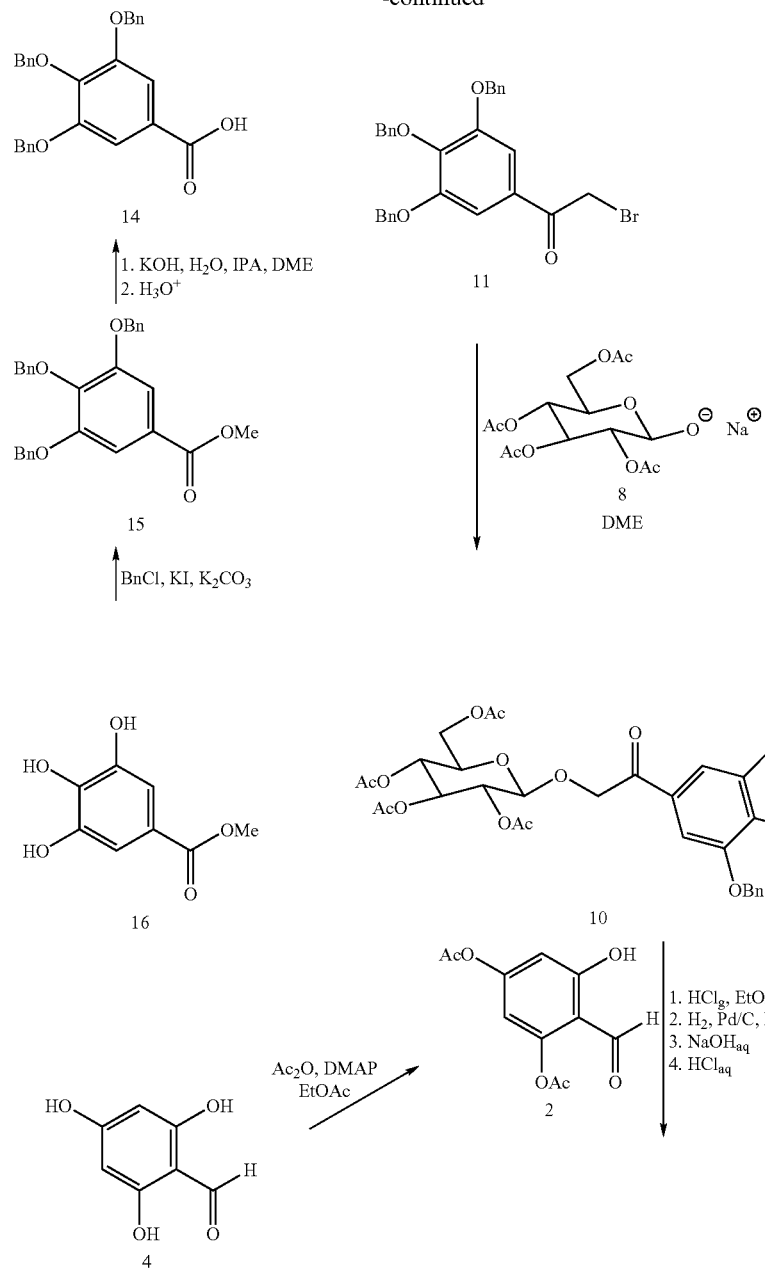
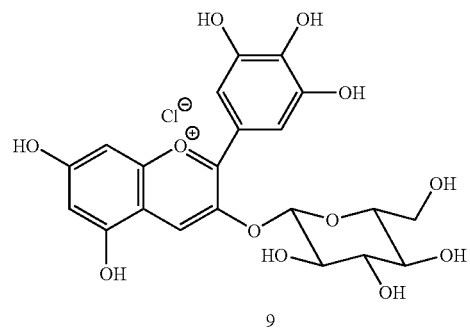

In Scheme 4, deprotection to give the final compound (9) involves removal of the benzyl and acetyl protecting groups present in compounds (2) and (10). It has been found that the order of removal of the protecting groups is important in order to optimise the yield of the product. Removal of the acetate protecting groups may be carried out using aqueous sodium hydroxide, whilst the benzyl groups are deprotected via hydrogenation. Removal of the acetate protecting groups first, before removal of the benzyl groups, tends to lead to decomposition of the product, whereas removal of the benzyl groups first followed by treatment with sodium hydroxide to remove the acetate groups gives good yields of the product (9). It is postulated that this difference is due to the differing tendencies of the various partially deprotected intermediates involved to decompose under basic conditions.

An alternative, preferred synthetic route to cyanidin-3-O-β-glucopyranoside chloride (1) uses iodide as the leaving group in the coupling reaction to form compound (3). In this method, compound (6) is converted to the corresponding iodide (19). The iodide (19) is unstable at higher temperatures, so the reaction conditions should be chosen to minimise any decomposition of the product. Suitable reaction conditions comprise stirring with sodium iodide in dry acetonitrile at room temperature overnight.

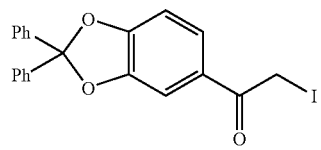

19

Compound (19) is then reacted with compound (8) in DCM to give compound (3) in significantly higher yield than the coupling of (5) with (8). Overall, the synthetic route via the iodo compound (19) is preferred due to the high yield of the coupling step between compound (19) and compound (8).

It is also possible to synthesize compound (1) using benzyl protecting groups for the OH groups in the S-1 compounds instead of the diphenylmethylene protecting group shown in Scheme 3. The use of benzyl protecting groups is particularly preferred for large scale synthesis due to their easy removal via hydrogenation (e.g. using hydrogen gas with a Pd/C catalyst).

It has been found that synthesis of delphinidin-3-O-β-glucopyranoside chloride (9) via the iodo compound (20) also results in better yields than using the bromo compound (11) as shown in Scheme 4.

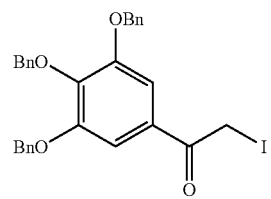

20

Compound (20) can be synthesised from compound (11) by halide exchange, for example by treatment with NaI in acetonitrile at room temperature. As with compound (19), the reaction conditions should be chosen to minimise decomposition of the product iodide (20), which is unstable at elevated temperatures. Alternatively, and preferably, compound (20) may be synthesized directly from compound (12) using N-iodosuccinamide (NIS) in dry THF. Compound (20) is then reacted with compound (8) in DCM to form compound (10) in high yields. It has been found that the overall yield of delphinidin-3-O-β-glucopyranoside chloride (9) can be improved by first converting compound (11) into compound (20), and then subsequently coupling this iodo-compound with compound (8) to form compound (10), despite the fact that this requires an additional synthetic step. The improvement in yield is due to the efficient coupling reaction between compound (20) and compound (8). Yields are further improved by converting compound (12) directly into compound (20) using NIS.

The tosylate analogue of compounds (11) and (20) may also be used as an intermediate in Scheme 4. This can be formed directly from compound (13) using Koser's reagent. The tosylate can then be used in the coupling reaction with compound (8) to form compound (10).

Anthocyanins comprising other aglycone cores can be made using analogous methodology to that shown in Schemes 3 and 4. For example, pelargonidin anthocyanins made be synthesized from the commercially available starting material 4-hydroxyacetophenone, peonidin anthocyanins from the commercially available starting material 4-hydroxy-3-methoxyacetophenone and malvidin anthocyanins from commercially the available starting material 3,5-dimethoxy-4-hydroxyacetophenone. Petunidin anthocyanins may be synthesized from a protected form of 3,4-dihydroxy-5-methoxyacetophenone (17), which may itself be synthesized from the commercially available starting material 3,4,5-trihydroxybenzoic acid (18) as shown below (Scheme 5).

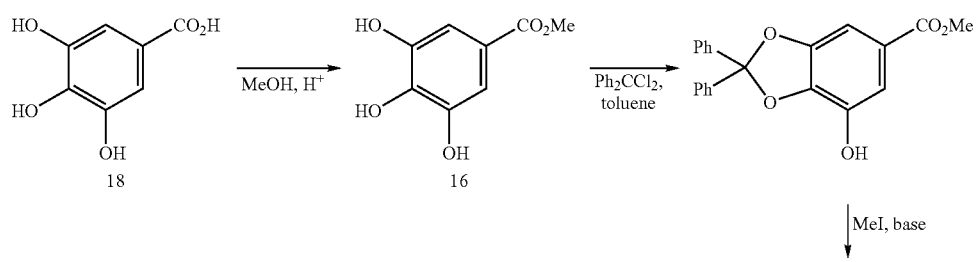

Scheme 5

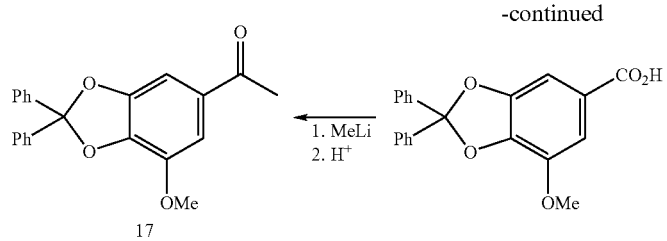
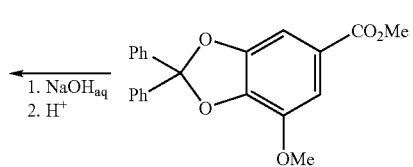

Any and all combinations of the preferred features referred to herein form part of the invention, whether or not such combinations are specifically disclosed.

The following Examples are non-limiting illustrations of the invention.

EXPERIMENTAL DETAILS

Nuclear magnetic resonance 300 MHz $^1$H-NMR spectra and 75 MHz $^{13}$C-NMR spectra were recorded on a Varian 300 MHz spectrometer. Tetramethylsilane (TMS) was used as internal reference. Chemical shifts of $^1$H-NMR spectra are reported downfield in ppm from TMS. $^{13}$C-NMR spectra are referenced in ppm to deuterochloroform ($\delta$=76.9 ppm) or to DMSO-$d_6$ ($\delta$=39.5 ppm) or to MeOH-$d_4$ ($\delta$=49.0 ppm). High pressure/performance liquid chromatography HPLC analyses were performed on a Waters 2695 (separation module) connected with a Waters 996 (photodiode array detector). The column used was a Hewlett Packard, HP ODS Hypersil (4.6× 200 mm, particle size 5 µm). The eluant was water-acetonitrile. Mass spectrometry (MS) analyses were performed on a Micromass Platform LCZ mass spectrometer using electrospray ionisation operating in positive mode. Dry flash chromatography was carried out with silica gel (Fluka: silica gel 60, particle size 0.040-0.063 mm (230-400 mesh)). Vacuum was created by a water aspirator. Thin layer chromatography (TLC) was carried out using silica gel plates from Fluka (silica gel/dc-alufolien-kieselgel with fluorescent indicator, prod.-no 60778). The spots were detected by UV (extinction at $\lambda$=254 nm or fluorescence at $\lambda$=366 nm) in a UVP-UV-cabinet and/or staining with MOP (molybdato phosphoric acid (14 g) in ethanol (125 ml)) or CER-MOP (molybdato phosphoric acid (5 g), cerium(IV)sulfate (2 g) and 98% $H_2SO_4$ (16 ml) in water (180 ml)) and developed by heating with a heat gun until spots appeared. Thin layer chromatography on anthocyanins was carried out on cellulose sheets (Merck, 1.05565, cellulose F) using FHW (98% formic acid-37% HCl-water, 4:1:8) as eluant. Commercially available chemicals were purchased from Fluka, Aldrich, Acros, Merck and Lancaster. Standard purification methods were applied if necessary. Dry acetone, acetonitrile DCM, DMSO, THF, DME and dry EtOAc were additionally purchased from Fluka.

2,4-Diacetoxy-6-hydroxybenzaldehyde (2)

2,4,6-Trihydroxybenzaldehyde (4) (4.62 g, 30 mmol), acetic anhydride (6.13 g, 60 mmol) and a catalytic amount of N,N-dimethylaminopyridine (DMAP) in dry ethyl acetate (EtOAc) (100 mL) were refluxed overnight. The reaction mixture was filtered, water (50 mL) was added and the water phase extracted with EtOAc (4×25 mL). The combined organic phases were washed with water (2×25 mL) and dried (MgSO$_4$). The crude product was recrystallized from 1,2-dimethoxyethane (DME) to give the titled compound as white crystals, m.p. 103-105° C. Yield 4.3 g. (60%). $^1$H NMR (300 MHz, CDCl$_3$): $\delta$=2.29 (3H, s), 2.36 (3H, s), 6.61 (1H, s), 6.63 (1H, s), 10.04 (1H, s), 11.77 (1H, s); $^{13}$C NMR (75 MHz): $\delta$=20.6 (CH$_3$), 21.0 (CH$_3$), 107.6 (CH), 108.1 (CH), 111.0 (C), 153.5 (C), 157.2 (C), 163.9 (C), 169.7 (C=O), 168.1 (C=O), 191.8 (HCO).

2-Chloro-3',4'-diphenylmethylenedioxyacetophenone (6)

2-Chloro-3',4'-dihydroxyacetophenone (7) (9.33 g, 50 mmol) was dissolved in toluene (125 mL), and α,α-dichlorodiphenylmethane (11.86 g, 50 mmol) was added. The reaction mixture was refluxed for 24 hours, cooled to room temperature and washed with water (6×20 mL). The water phase was extracted with toluene (3×50 mL) and the combined organic phases dried (MgSO$_4$). Filtration and evaporation of the solvent left a yellow solid which was essentially pure product. Recrystallisation from a mixture of petroleum ether and ethyl acetate gave the titled compound as white crystals, m.p. 100-101° C. Yield 15.7 g (89%); $^1$H NMR (300 MHz, CDCl$_3$): $\delta$=4.55 (2H, s), 6.89 (1H, d, J=8.7 Hz), 7.34-5.57 (12H, m); $^{13}$C NMR (75 MHz): $\delta$=45.5 (CH$_2$), 108.1 (2×CH), 108.2 (C), 118.4 (C), 124.9 (CH), 126.0 (2×CH), 128.2 (4×CH), 128.8 (C), 129.3 (4×CH), 139.2 (2×C), 147.8 (C), 151.8 (C), 189.0 (C=O).

2-Bromo-3',4'-diphenylmethylenedioxyacetophenone (5)

2-Chloro-3',4'-diphenylmethylenedioxyacetophenone (6) (7.02 g, 20 mmol) was dissolved in dry acetone (150 mL) and sodium bromide (2.26, 22 mmol) was added. The reaction mixture was refluxed overnight. Filtration and evaporation of the solvent left a yellow solid which was essentially pure product. Recrystallisation from a mixture of petroleum ether and ethyl acetate gave the titled compound as white crystals, m.p. 78-79° C. Yield 7.71 g (97%); $^1$H NMR (300 MHz, CDCl$_3$): $\delta$=4.34 (2H, s), 6.93 (1H, d), 7.34-7.52 (12H, m); $^{13}$C NMR (75 MHz): $\delta$=30.5 (CH$_2$), 108.1 (2×CH), 108.6 (C), 118.4 (C), 125.5 (C), 126.0 (2×CH), 128.1 (4×CH), 128.4 (C), 129.3 (4×CH), 139.3 (2×C), 147.9 (C), 151.9 (C), 189.4 (C=O).

2-Iodo-3',4'-diphenylmethylenedioxyacetophenone (19)

2-Chloro-3',4'-diphenylmethylenedioxyacetophenone (6) (52.62 g, 0.15 mol) and sodium iodide (34.47 g, 0.23 mol) were dissolved in dry acetonitrile (400 mL) and stirred at room temperature overnight. The solution was filtered and acetonitrile removed under vacuum. Water (200 mL) was added and the solution was extracted with diethyl ether (4×150 mL). The organic phase was dried (MgSO$_4$) and the solvents removed in vacuo. Recrystallisation from methylcyclohexane afforded the titled compound as yellow crystals, m.p. 105-107° C. Yield 65.0 g (98%). $^1$H NMR (300 MHz, CDCl$_3$) δ=4.26 (s, 2H), 6.91-7.04 (m, 2H), 7.26-7.30 (m, 5H), 7.42-7.50 (m, 6H); $^{13}$C NMR (75 MHz, CDCl$_3$) δ=1.3 (CH$_2$), 108.1 (2×CH), 108.7 (C), 118.4 (C), 125.5 (C), 126.1 (2×CH), 128.0 (C), 128.3 (4×CH), 129.3 (4×CH), 139.3 (2×C), 147.9 (C), 151.7 (C), 191.0 (C=O).

2-(2,3,4,6-Tetra-O-acetyl-β-D-glucopyranosyloxy)-3',4'-diphenylmethylenedioxyacetophenone (3)

Method A:

2-Bromo-3',4'-diphenylmethylenedioxyacetophenone (5) (1.98 g, 5 mmol) and β-D-glucose-2,3,4,6-tetraacetate (8) (C. M. McCloskey, G. H. Coleman, Organic Syntheses, Coll. Vol. 3 434) (1.74 g, 5 mmol) was dissolved in dry DCM (50 mL) and sodium hydride (0.18 g, 7.5 mmol (0.3 g 60% NaH suspension in oil)) was added in small portions. The reaction mixture was stirred at room temperature overnight. Water (50 mL) was added and the water phase extracted with DCM (3×25 mL). The organic layers were combined and washed with water (2×50 mL), dried (MgSO$_4$) and evaporated to give a yellow oil. The crude product was isolated by dry flash chromatography (PE/EtOAc 6:4) (PE=petroleum ether) to give 1.22 g (37%) of a yellow viscous oil which slowly solidified upon standing. Repeating the reaction using dry tetrahydrofuran (THF) as solvent in place of DCM resulted in a yield of 51%. Repeating the reaction using dry DME as solvent resulted in a yield of 63%. $^1$H NMR (300 MHz, CDCl$_3$): δ=1.90 (3H, s), 1.92 (3H, s), 1.94 (3H, s), 1.95 (3H, s), 4.01-4.07 (2H, m), 4.61-4.75 (5H, m), 5.01-5.10 (1H, m), 5.15-5.25 (1H, m), 6.80 (1H, d, J=8.4 Hz), 7.27-7.48 (12H, m); $^{13}$C NMR (75 MHz): δ=20.4 (4×CH$_3$), 61.5 (CH$_2$), 68.0 (CH$_2$), 70.1 (CH), 70.7 (CH), 71.6 (CH), 72.3 (CH), 99.9 (CH), 107.8 (2×CH), 108.0 (C), 118.4 (C), 124.3 (CH, C), 125.9 (2×CH), 128.1 (4×CH), 128.2 (C), 129.2 (4×CH), 139.2 (2×C), 147.5 (C), 151.4 (C), 169.1 (C=O), 169.4 (C=O), 169.8 (C=O), 170.3 (C=O), 192.6 (C=O).

Method B:

2-Iodo-3',4'-diphenylmethylenedioxyacetophenone (19) (6.63 g, 15 mmol) and β-D-glucose-2,3,4,6-tetraacetate (8) (6.27 g, 18 mmol) was dissolved in dry DCM (50 mL) and sodium hydride (0.72 g, 30 mmol (1.2 g 60% NaH suspension in oil)) was added in small portions. The reaction mixture was stirred at room temperature overnight. Excess of sodium hydride was decomposed by addition of a suitable amount water. Dichloromethane was removed under vacuum. Water (100 mL) was added and the water phase extracted with diethyl ether (4×75 mL). The organic layers were combined and washed with water (2×50 mL), dried (MgSO$_4$) and evaporated to give a dark oil. The crude product was isolated by dry flash chromatography (PE/EtOAc 6:4) to give 7.26 g (73%) of a pale yellow solid.

Cyanidin 3-O-β-glucopyranoside chloride (1)

2,4-Diacetoxy-6-hydroxybenzaldehyde (2) (0.38 g, 1.58 mmol) and 2-(2,3,4,6-tetra-O-acetyl-β-D-glucopyranosyloxy)-3',4'-diphenylmethylenedioxyacetophenone (3) (1.05 g, 1.58 mmol) were dissolved in dry EtOAc (75 mL) and dry HCl (g) (generated by action of 98% H$_2$SO$_4$ on solid NaCl) was bubbled through the solution for several hours. The reaction was stirred at room temperature overnight, and the reaction mixture went from colourless to deep red after some hours. TLC showed that all the starting materials were consumed, and two products formed. Co-elution with benzophenone confirmed the identity of the less polar product and showed that deprotection had occurred. The EtOAc was evaporated and the crude product was dissolved in a small amount of acidified MeOH. Complete deacetylation was performed by treatment with NaOH (2 M). The solution turned blue-green. When the hydrolysis was complete HCl (2 M) was added until the solution turned red again. MeOH was evaporated, and the product was dissolved in HCl$_{aq}$ (0.1%) and extracted with EtOAc to remove benzophenone. The water layer was concentrated in vacuo and the residue eluted with water through an Amberlite XAD-7 column to remove the acetic acid formed in the hydrolysis reaction. The anthocyanin was finally eluted with acidified MeOH. Careful evaporation of the solvent left a red black solid which was essentially pure product. Yield 0.73 g (95%). The target molecule was identical by the usual criteria (TLC, HPLC, MS, $^1$H-NMR, $^{13}$C-NMR) with an authentic sample. $^1$H NMR (300 MHz, CD$_3$OD, 10% CF$_3$COOD): δ=3.45-3.88 (6H, m), 5.26 (1H, d, J=7.7 Hz), 6.58 (1H, s (broad), 6.80 (1H, d, J=1.8 Hz), 6.89 (1H, d, J=8.7 Hz), 7.89 (1H, d, J=2.3 Hz), 8.09 (1H, dd, J=2.3 Hz, J=8.7 Hz), 8.85 (1H, s); $^{13}$C NMR (75 MHz): δ=62.8 (CH$_2$), 72.5 (CH), 75.3 (CH), 77.5 (CH), 78.6 (CH), 95.5 (CH), 103.7 (CH), 103.9 (CH), 113.4 (C), 116.1 (CH), 118.1 (CH), 121.3 (C), 127.5 (CH), 136.6 (CH), 145.7 (C), 147.4 (C), 155.9 (C), 158.9 (C), 159.4 (C), 163.8 (C), 170.6 (C). ESI-MS: m/z=449 [MCl—Cl].$^{+1}$H-NMR, $^{13}$C-NMR in accordance with T. Fossen, Ø. M. Andersen, D. O. Øvstedal, A. T. Pedersen, Å, Raknes, J. Food Sci. 1996, 61, 703.

Methyl 3,4,5-tribenzyloxybenzoate (15)

Method A:

Methyl 3,4,5-trihydroxybenzoate (16) (55.24 g, 0.3 mol), benzyl chloride (113.93 g, 0.9 mol), dry potassium carbonate (124.39 g, 0.9 mol) and potassium iodide (catalytic amount) were stirred in refluxing dry acetone (600 mL) for 12 h. After cooling, the acetone was evaporated, and the solution was dissolved in water (250 mL). The water phase was extracted with diethyl ether (4×100 mL), the organic phase was washed with brine (2×50 mL), dried (MgSO$_4$) and the solvent was removed in vacuo. Recrystallisation from petroleum ether and ethyl acetate gave the titled compound as white crystals, m.p. 102-103° C. Yield: 121.4 g (89%). Spectroscopic data were in accordance with the literature (J. Barbera, R. Iglesias, J. L. Serrano, T. Sierra, M. R. de la Fuente, B. Palacios, M. A. Perez-Jubindo, J. T. Vazquez, J. Am. Chem. Soc. 1998, 120, 2908).

Method B:

Methyl 3,4,5-trihydroxybenzoate (16) (55.24 g, 0.3 mol), benzyl chloride (113.93 g, 0.9 mol), potassium carbonate (124.39 g, 0.9 mol) and potassium iodide (catalytic amount) were mechanically stirred in dry DMSO (200 mL) at room temperature overnight. Water (200 mL) was added and the crude product isolated by filtration. Evaporation of residual solvents in a vacuum desiccator left a pale yellow solid which was essentially pure product. Yield: 128.2 g (94%).

3,4,5-Tribenzyloxybenzoic acid (14)

To a mixture of methyl 3,4,5-tribenzyloxybenzoate (15) (20.60 g, 45.30 mmol) in 2-propanol (200 mL) was added a solution of potassium hydroxide (3.50 g, 85%, 53.00 mmol) in 2-propanol (25 mL). The mixture was refluxed for 1 h, cooled, and water was added (250 mL). A white precipitate appeared, and the mixture was filtered. Recrystallisation from ethyl acetate afforded the desired compound as white crystals, m.p. 194-195° C. Yield: 17.2 g (86%). $^1$H NMR (300 MHz, DMSO-d$_6$): δ=5.05 (2H, s), 5.18 (4H, s), 7.24-7.50

(17H, m), 13.4 (1H, s, broad); $^{13}$C NMR (75 MHz): δ=70.3, 74.3, 108.3, 126.1, 127.7, 128.0, 128.2, 128.3, 128.5, 136.9, 137.5, 141.0, 152.1, 167.0.

3,4,5-Tribenzyloxyacetophenone (13)

To a solution of 3,4,5-tribenzyloxybenzoic acid (14) (11.01 g, 25.0 mmol) in dry DME (1 L), methyllithium (36.6 mL, 1.5 M, 55.0 mmol) was added at 0° C. The mixture was stirred for 1 h, then water (150 mL) was added. The mixture was extracted with diethyl ether (2×250 mL), the organic phase washed with brine (2×50 mL), dried (MgSO$_4$), and the solvents were removed in vacuo. Recrystallisation from petroleum ether and ethyl acetate provided the titled compound as white crystals, m.p. 116-117° C. Yield: 10.2 g (93%) $^1$H NMR (300 MHz, CDCl$_3$): δ=2.49 (3H, s), 5.14 (6H, s), 7.23-7.48 (17H, m); $^{13}$C NMR (75 MHz): δ=26.3, 71.3, 75.1, 108.2, 127.4, 127.8, 127.9, 128.1, 128.4, 132.3, 136.5, 137.2 (C) 142.8, 152.5, 196.7.

1-Acetoxy-1-(3',4',5'-tribenzyloxy)phenylethene (12)

3,4,5-Tribenzyloxyacetophenone (13) (4.38 g, 10.0 mmol) and p-toluene sulfonic acid (cat. amount) were dissolved in isopropenyl acetate (100 mL) and heated until a distillate appeared. The heating of the mixture was continued until all acetone generated in the reaction was removed. Then water (50 mL) was added. The organic phase was separated from the water phase, and the latter was extracted with diethyl ether (3×50 mL). The combined organic phases were dried (MgSO$_4$) and the solvents removed in vacuo. Recrystallisation from a mixture of petroleum ether and ethyl acetate afforded the desired compound as pale brown crystals, m.p. 99-100° C. Yield: 4.50 g (87%); $^1$H NMR (300 MHz, CDCl$_3$): δ=2.14 (3H, s), 4.93 (1H, d, J=2.1 Hz), 5.06 (2H, s), 5.11 (4H, s), 5.29 (1H, d, J=2.1 Hz), 6.73 (2H, s), 7.20-7.50 (15H, m). $^{13}$C NMR (75 MHz): δ=20.7, 71.3, 75.1, 101.7, 105.1, 127.2, 127.4, 127.7, 127.8, 127.9, 128.0, 128.4, 128.5, 129.8, 136.8, 152.7, 168.8.

2-Bromo-3',4',5'-tribenzyloxyacetophenone (11)

1-Acetoxy-1-(3',4',5'-tribenzyloxy)-phenylethene (12) (4.80 g, 10.0 mmol), N-bromosuccinimide (2.67 g, 15 mmol) and water (0.27 g, 15 mmol) were dissolved in THF (100 mL) and stirred overnight. Water (50 mL) was then added. The organic phase was separated from the water phase, and the latter was extracted with diethyl ether (3×50 mL). The combined organic phases were dried (MgSO$_4$) and the solvents removed in vacuo. Recrystallisation from a mixture of petroleum ether and ethyl acetate afforded the desired compound as white crystals, m.p. 112-113° C. Yield: 4.91 g (95%). $^1$H NMR (300 MHz, CDCl$_3$) δ=4.29 (s, 2H), 5.14 (s, 2H), 5.16 (s, 4H), 7.24-7.46 (m, 17H). $^{13}$C NMR (75 MHz) δ=30.3, 71.3, 75.1, 108.9, 127.4, 127.9, 128.0, 128.1, 128.4, 128.5, 128.9, 136.3, 137.1, 152.4, 152.6, 190.0.

2-Iodo-3',4',5'-tribenzyloxyacetophenone (20)

Method A:
2-Bromo-3',4',5'-tribenzyloxyacetophenone (5.17 g, 10.0 mmol) (11) and sodium iodide (2.25 g, 15 mmol) were dissolved in dry acetonitrile (50 mL) and stirred at room temperature overnight. The solution was filtered and acetonitrile removed under vacuum. Water (30 mL) was added and the solution was extracted with diethyl ether (4×25 mL). The organic phase was dried (MgSO$_4$) and the solvents removed in vacuo. Recrystallisation from methylcyclohexane afforded the titled compound as yellow crystals, m.p. 110-112° C. Yield 3.6 g (64%). $^1$H NMR (300 MHz, CDCl$_3$): δ=4.21 (2H, s), 5.15 (6H, s), 7.22-7.48 (17H, m); $^{13}$C NMR (75 MHz): δ=1.0, 71.3, 75.1, 109.0, 127.4, 127.9, 128.0, 128.1, 128.3, 128.4, 128.5, 136.3, 137.1, 143.4, 152.6, 191.5.

Method B:
1-Acetoxy-1-(3',4',5'-tribenzyloxy)-phenylethene (12) (4.80 g, 10 mmol) and N-iodosuccinimide (2.25 g, 10 mmol) were dissolved in dry THF (100 mL) and stirred overnight. More N-iodosuccinimide (2.25 g, 10 mmol) was added and the reaction mixture stirred at room temperature until TLC showed that the vinyl acetate was consumed. Tetrahydrofuran was removed under vacuum. Water (75 mL) was then added. The organic phase was separated from the water phase, and the latter latter was extracted with diethyl ether (4×50 mL). The combined organic phases were dried (MgSO$_4$) and the solvents removed in vacuo. Recrystallisation from a mixture of petroleum ether and ethyl acetate afforded the desired compound as white crystals, m.p. 110-112° C. Yield: 5.2 g (92%).

2-(2,3,4,6-Tetra-O-acetyl-β-D-glucopyranosyloxy)-3',4',5'-tribenzyloxyacetophenone (10)

Method A:
2-Bromo-3',4',5'-tribenzyloxyacetophenone (11) (2.59 g, 5 mmol) and β-D-glucose-2,3,4,6-tetraacetate (8) (1.74 g, 5 mmol) were dissolved in dry DME (50 mL) and sodium hydride (0.18 g, 7.5 mmol) (0.3 g 60% NaH suspension in oil) was added in small portions. The reaction mixture was allowed to be stirred at room temperature overnight. Water (50 mL) was added and the water phase extracted with DCM (3×25 mL). The organic layers were combined and washed with water (2×50 mL), dried (MgSO$_4$) and evaporated to give a dark viscous oil. The product was isolated by dry flash chromatography (PE/EtOAc 6:4) (PE=petroleum ether). Recrystallisation from a mixture of methylcyclohexane and ethyl acetate afforded the desired compound as white crystals, m.p. 156-158° C. Yield 0.51 g (13%). $^1$H NMR (300 MHz, CDCl$_3$): δ=1.98 (3H, s), 2.00 (3H, s), 2.02 (3H, s), 2.06 (3H, s), 3.63-3.73 (2H, m), 4.08-4.30 (5H, m), 4.62-4.94 (1H, m), 5.02-5.34 (7H, m), 7.20-7.56 (17H, m); $^{13}$C NMR (75 MHz): δ=20.5, 20.6, 61.6, 68.2, 70.5, 70.8, 71.2, 71.8, 72.4, 75.0, 100.1, 107.9, 127.4, 127.9, 128.0, 128.1, 128.4, 128.5, 129.6, 136.4, 137.1, 143.2, 152.6, 169.3, 169.5, 170.0, 170.5, 193.4.

Method B:
2-Iodo-3',4',5'-tribenzyloxyacetophenone (20) (5.64 g, 10 mmol) and β-D-glucose-2,3,4,6-tetraacetate (8) (4.18 g, 12 mmol) was dissolved in dry DCM (50 mL) and sodium hydride (0.48 g, 20 mmol) (0.8 g 60% NaH suspension in oil)) was added in small portions. The reaction mixture was allowed to be stirred at room temperature overnight. Excess of sodium hydride was decomposed by addition of suitable amount water. Dichloromethane was removed under vacuum in order to simplify the work up. Water (100 mL) was added and the water phase extracted with diethyl ether (4×75 mL). The organic layers were combined and washed with water (2×50 mL), dried (MgSO$_4$) and evaporated to give a dark viscous oil. The product was isolated by dry flash chromatography (PE/EtOAc 6:4). Recrystallisation from a mixture of methylcyclohexane and ethyl acetate afforded the desired compound as white crystals, m.p. 156-158° C. Yield 5.1 g (65%).

Delphinidin 3-O-β-glucopyranoside chloride (9)

2,4-Diacetoxy-6-hydroxybenzaldehyde (2) (0.38 g, 1.58 mmol) and 2-(2,3,4,6-tetra-O-acetyl-β-D-glucopyranosyloxy)-3', 4', 5'-tribenzyloxyacetophenone (10) (1.24 g, 1.58 mmol) were dissolved in dry EtOAc (75 mL) and dry HCl (g) (generated by action of 98% $H_2SO_4$ on solid NaCl) was bubbled through the solution for several hours. The reaction was stirred at room temperature overnight, and the reaction mixture went from colourless to deep red after some hours. The reaction mixture was stirred at room temperature until TLC showed that all the starting materials were consumed. The EtOAc was evaporated and the crude product was dissolved in a small amount of acidified MeOH. The benzyl groups were removed by hydrogenation ($H_2$ 1 atm. 10% Pd/C) at room temperature. The course of the reaction was monitored by TLC. The catalyst was removed by filtration and the reaction mixture was kept in acidified MeOH under nitrogen. Complete deacetylation was performed by treatment with NaOH (2 M). The solution turned blue-green. When the hydrolysis was complete HCl (2 M) was added until the solution turned red again. MeOH was evaporated, and the product was dissolved in $HCl_{aq}$ (0.1%) and extracted with EtOAc to remove traces of toluene. The water layer was concentrated on in vacuo and the residue eluted with water through an Amberlite XAD-7 column to remove the acetic acid formed in the hydrolysis reaction. The product (9) was finally eluted with acidified MeOH. Careful evaporation of the solvent left a red black solid which was essentially pure product (9). Yield 0.65 g (82%). The target molecule was identical by the usual criteria (TLC, HPLC, MS, $^1$H-NMR, $^{13}$C-NMR) with an authentic sample. $^1$H NMR (300 MHz, $CD_3OD$, 10% $CF_3COOD$ δ=3.45-3.88 (6H, m), 5.32 (1H, d, J=7.6 Hz), 6.61 (1H, d, J=2.0 Hz), 6.81 (1H, broad d, J=2.0 Hz), 7.70 (2H, s), 8.90 (1H, s); $^{13}$C NMR (75 MHz): δ=62.7 ($CH_2$), 71.0 (CH), 75.1 (CH), 77.9 (CH), 79.1 (CH), 95.6 (CH), 102.8 (CH), 104.0 (CH), 112.6 (2×CH), 113.6 (C), 121.0 (C), 136.4 (CH), 145.0 (C) 146.6 (C), 147.9 (2×C), 158.0 (C) 159.3 (C), (C), 121.0 (C), 136.4 (CH), 145.0 (C) 146.6 (C), 147.9 (2×C), 158.0 (C) 159.3 (C), 164.0 (C), 170.2 (C). ESI-MS: m/z=465 [MCl—Cl]. $^1$H-NMR, $^{13}$C-NMR in accordance with T. Tsuda, K. Ohshima, S. Kawakishi, T. Osawa, *J. Agric. Food Chem.* 1994, 42, 248.

The invention claimed is:

1. A method for preparing an Eastern portion of an anthocyanin, comprising:

reacting an α-functionalized ketone starting material of general formula S-1:

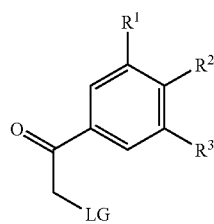

S-1 wherein LG is a leaving group;
$R^1$ is H, OMe or OPG;
$R^2$ is OPG;
$R^3$ is H, OMe or OPG; and
each PG independently denotes a protecting group such that where PG is present in different parts of a compound it may, but does not necessarily, denote the same protecting group; and two adjacent OPG groups may optionally be taken together to form a cyclic moiety;
with a sugar anion of general formula:
XO⁻ wherein XO⁻ is an anion formed by removal of a proton from an anomeric oxygen atom of a sugar, any other hydroxy groups of the sugar being protected by suitable protecting groups; and optionally removing some or all of the protecting groups;

to give an Eastern half intermediate of general formula E-1:

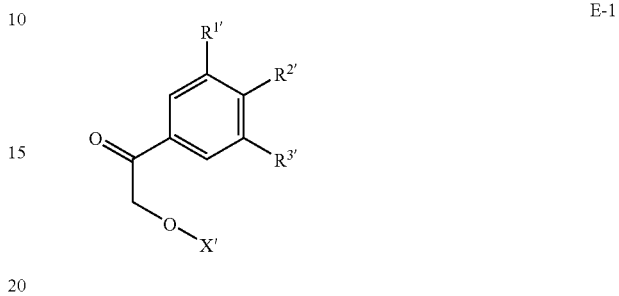

E-1 wherein $R^{1'}$, $R^{2'}$, $R^{3'}$ and X' are each independently the same as $R^1$, $R^2$, $R^3$ and X respectively, or are their deprotected analogues.

2. The method as claimed in claim 1 wherein LG is Br or I.

3. The method as claimed in claim 1 wherein the sugar from which XO⁻ is derived is glucose or rutinose.

4. The method as claimed in claim 1 wherein XO⁻ is prepared in situ by reaction of XOH with a hydride reagent.

5. The method as claimed in claim 4 wherein the hydride reagent is sodium hydride.

6. The method as claimed in claim 1 wherein each PG group is independently selected from acetyl, benzyl and benzoyl and/or two adjacent OPG groups together denote diphenylmethylenedioxy.

7. The method as claimed in claim 1 wherein a solvent in which the reaction is carried out is tetrahydrofuran (THF), 1,2-dimethoxyethane (DME) or dichloromethane (DCM).

8. A method for preparing an anthocyanin, comprising the method as claimed in claim 1 for preparing an Eastern portion of an anthocyanin followed by:

optionally, in the event that any of $R^{1'}$, $R^{2'}$, $R^{3'}$ or X' are the deprotected analogues of $R^1$, $R^2$, $R^3$ or X respectively, reprotecting one or more of $R^{1'}$, $R^{2'}$, $R^{3'}$ and X'; and then reacting the Eastern half intermediate of general formula E-1 or its reprotected derivative, with a Western half intermediate of general formula W-1:

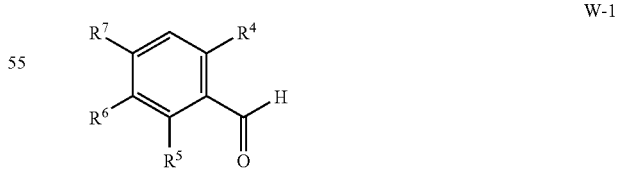

W-1 wherein either $R^4$ is OH, $R^5$ is OPG, $R^6$ is H, and $R^7$ is OH or OPG;

or $R^4$ is OH, $R^5$ is H, $R^6$ is OH or OPG, and $R^7$ is H;

thereby coupling intermediates E-1 and W-1, and optionally removing one, several or all protecting groups, to provide an anthocyanin product of general formula P-1:

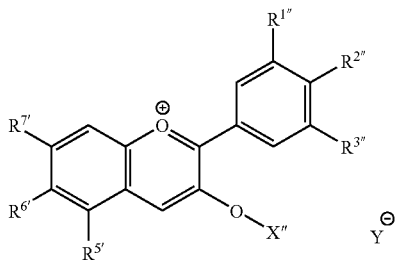

P-1

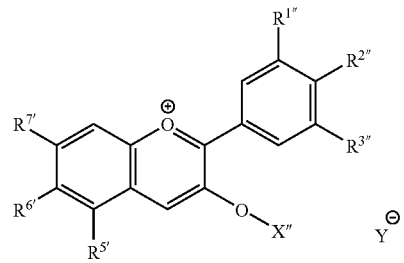

P-1 wherein $R^{1'''}$, $R^{3'''}$, $X''$, $R^5$, $R^{6'}$ and $R^{7'}$ are each independently the same as $R^{1'}$, $R^{2'}$, $R^{3'}$, $X'$, $R^5$, $R^6$ and $R^7$ respectively, or are their deprotected analogues; and $Y^-$ is a counterion, preferably a physiologically acceptable counterion.

9. The method as claimed in claim 8 wherein the anthocyanin product of general formula P-1 is a naturally occurring cyanidin or delphinidin anthocyanin.

10. A compound of general formula P-1:

wherein $R^{1'''}$ is H, OMe, OPG or a deprotected analogue; $R^{2'''}$ is OPG or a deprotected analogue; $R^{3'''}$ is H, OMe, OPG or a deprotected analogue; $X''$—O— is a sugar attached at an anomeric oxygen atom of the sugar, any other hydroxy groups of the sugar being optionally protected by suitable protecting groups; $Y^-$ is a counterion; and wherein $R^{5'}$ and $R^{7'}$ are H, and $R^{6'}$ is OH, O-acetyl, O-benzyl or O-benzoyl.

11. The compound of claim 10, wherein said counterion is a physiologically acceptable counterion.

\* \* \* \* \*